(12) United States Patent
Bujny et al.

(10) Patent No.: US 10,174,127 B2
(45) Date of Patent: Jan. 8, 2019

(54) HUMAN NEUTRALIZING ANTIBODIES BINDING TO INFLUENZA NEURAMINIDASE

(71) Applicant: Janssen Vaccines & Prevention B.V., Leiden (NL)

(72) Inventors: Miriam Verena Bujny, The Hague (NL); Remko Van Der Vlugt, Zoetermeer (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 15/548,919

(22) PCT Filed: Feb. 4, 2016

(86) PCT No.: PCT/EP2016/052363
§ 371 (c)(1),
(2) Date: Aug. 4, 2017

(87) PCT Pub. No.: WO2016/124682
PCT Pub. Date: Aug. 11, 2016

(65) Prior Publication Data
US 2018/0016348 A1    Jan. 18, 2018

(30) Foreign Application Priority Data
Feb. 5, 2015 (EP) .................................... 15153891

(51) Int. Cl.
| | |
|---|---|
| A61K 39/00 | (2006.01) |
| A61K 39/395 | (2006.01) |
| C07K 16/28 | (2006.01) |
| A61K 39/12 | (2006.01) |
| A61K 39/145 | (2006.01) |
| C07K 16/40 | (2006.01) |
| C07K 16/10 | (2006.01) |
| G01N 33/569 | (2006.01) |

(52) U.S. Cl.
CPC .......... *C07K 16/40* (2013.01); *C07K 16/1018* (2013.01); *G01N 33/56983* (2013.01); *C07K 2317/21* (2013.01); *C07K 2317/33* (2013.01); *C07K 2317/56* (2013.01); *C07K 2317/565* (2013.01); *C07K 2317/732* (2013.01); *C07K 2317/76* (2013.01); *C07K 2317/92* (2013.01); *G01N 2333/924* (2013.01); *G01N 2469/10* (2013.01)

(58) Field of Classification Search
CPC ............ C07K 2317/76; C07K 2317/24; C07K 16/1018; A61K 2039/505; A61K 2300/00
See application file for complete search history.

(56) References Cited

FOREIGN PATENT DOCUMENTS

| | | |
|---|---|---|
| CN | 102023212 A | 4/2011 |
| WO | 84/03564 A1 | 9/1984 |
| WO | 93/09872 A1 | 5/1993 |
| WO | 00/63403 A2 | 10/2000 |
| WO | 2007052242 A1 | 5/2007 |
| WO | 2008028946 A2 | 3/2008 |
| WO | 2013007770 A1 | 1/2013 |

OTHER PUBLICATIONS

Shoji et al. "An influenza N1 neuraminidase-specific monoclonal antibody with broad inhibition activity against H5N1 HPAI viruses", Human Vaccines, 7(1), 2011:199-204.*
Shoji et al. , "An influenza N1 neuraminidase-specific monoclonal antibody with broad neuraminidase inhibition activity against H5N1 HPAI viruses", Human Vaccines, 7(1), 2011:199-204.*
Int'l Search Report dated Apr. 15, 2016 in Int'l Application No. PCT/EP2016/052363.
Written Opinion dated Apr. 15, 2016 in Int'l Application No. PCT/EP2016/052363.
Brown and Laver, "The Effect of Antineuraminidase Antibody on the Elution of Influenza Virus from Cells," Journal of General Virology, vol. 2, 291-295 (1968).
Shoji et al, "An Influenza N1 Neuraminidase-Specific Monoclonal Antibody With Broad Neuraminidase Inhibition Activity Against H5N1 HPAI Viruses," Human Vaccines, pp. 199-204 (2011).
Kasel et al, "Effect of Influenza Anti-Neuraminidase Antibody on Virus Neutralization," Infection and Immunity, vol. 8, No. 1, pp. 130-131 (1973).
Findlay et al, "Appropriate Calibration Curve Fitting in Ligand Binding Assays," The AAPS Journal, vol. 9, No. 2, Article 29, pp. E260-E267 (2007).
Kabat et al, "Identical V Region Amino Acid Sequences and Segments of Sequences in Antibodies of Different Specificities: Relative Contributions of VH and VL Genes, Minigenes, and Complementarity-Determining Regions to Binding of Antibody-Combining Sites," The Journal of Immunology, vol. 147, No. 5, pp. 1709-1719 (1991).
Marissen et al, "Novel Rabies Virus-Neutralizing Epitope Recognized by Human Monoclonal Antibody: Fine Mapping and Escape Mutant Analysis," Journal of Virology, vol. 79, No. 8, pp. 4672-4678 (2005).

* cited by examiner

*Primary Examiner* — Barry A Chestnut
(74) *Attorney, Agent, or Firm* — Panitch Schwarze Belisario & Nadel LLP

(57) ABSTRACT

The present invention provides influenza neuraminidase (NA)-binding human antibodies, which are capable of neutralizing at least one influenza A virus strain comprising NA of the N1 subtype, and antigen-binding fragments thereof. In certain embodiments, the antibodies or antigen-binding fragments furthermore are capable of neutralizing at least one influenza A virus strain comprising NA of the N2 subtype. The invention furthermore relates to the use of said antibodies or antigen-binding fragments in the diagnosis, prophylaxis and/or treatment of influenza infection.

22 Claims, 1 Drawing Sheet
Specification includes a Sequence Listing.

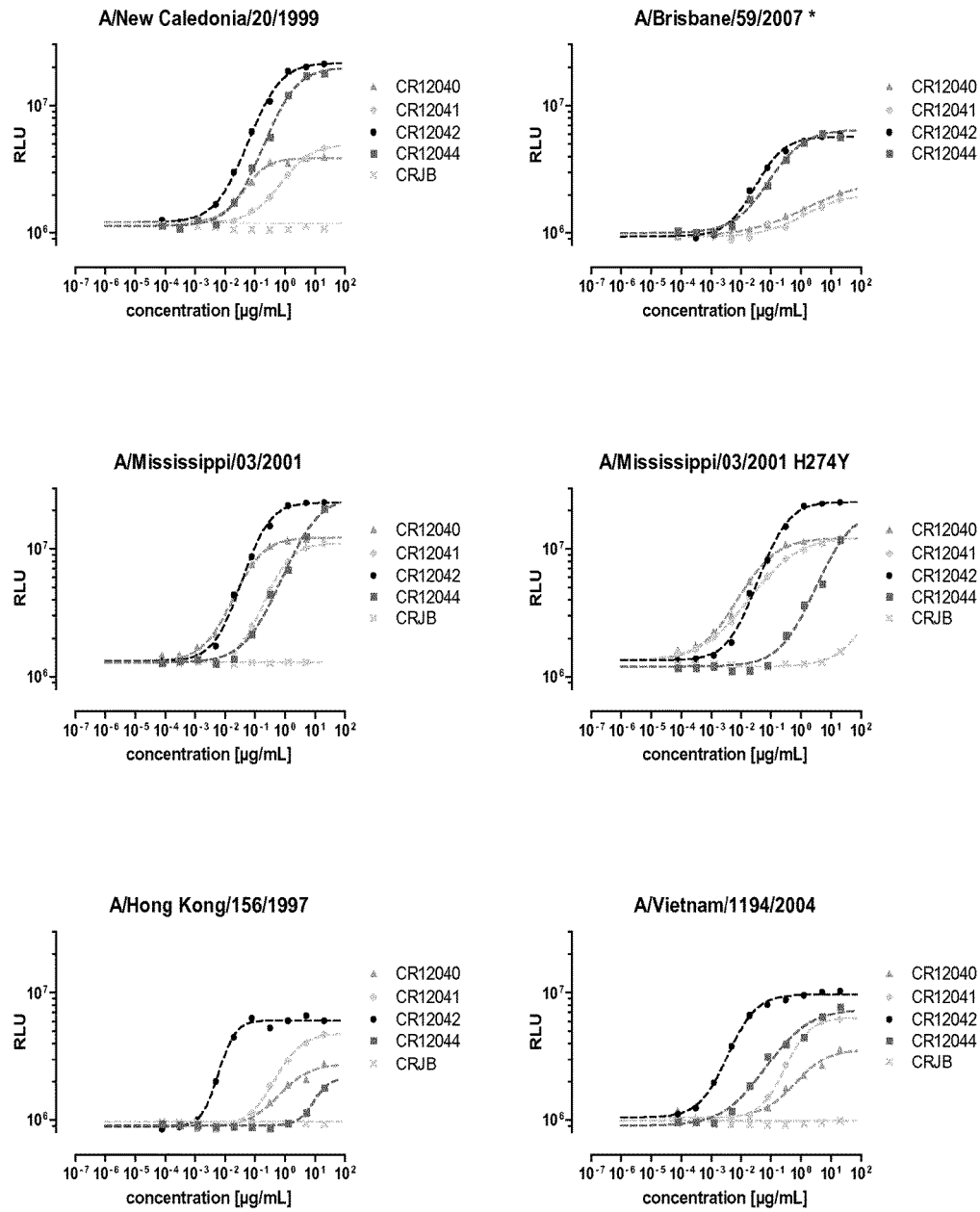

HUMAN NEUTRALIZING ANTIBODIES BINDING TO INFLUENZA NEURAMINIDASE

CROSS-REFERENCE TO RELATED APPLICATION

This application is a Section 371 of International Application No. PCT/EP2016/052363, filed Feb. 4, 2016, which was published in the English language on Aug. 11, 2016 under International Publication No. WO 2016/124682 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688097_347US", creation date of Aug. 4, 2017, and having a size of 14.0 KB. The sequence listing submitted via EFS-Web is part of the specification and is herein incorporated by reference in its entirety.

FIELD OF THE INVENTION

The invention relates to the field of medicine. This invention in particular relates to human antibodies against influenza, and more particularly to influenza neuraminidase (NA)-specific monoclonal antibodies and/or antigen-binding fragments thereof. The invention further relates to the diagnosis, prophylaxis and/or treatment of an influenza virus infection.

BACKGROUND OF THE INVENTION

Influenza infection (also referred to as "influenza" or "the flu") is a highly contagious disease with the potential to be devastating both in developing and developed countries. Influenza rapidly spreads in seasonal epidemics affecting 5-15% of the population and the burden on health care costs and lost productivity are extensive (World Healthcare Organization (WHO)).

There are three genera of influenza virus (types A, B and C) responsible for infectious pathologies in humans and animals. The type A and type B viruses are the agents responsible for the influenza seasonal epidemics (type A and B) and pandemics (type A) observed in humans.

Influenza A viruses can be classified into influenza virus subtypes based on variations in antigenic regions of two genes that encode the surface glycoproteins hemagglutinin (HA) and neuraminidase (NA) which are required for viral attachment and cellular release, respectively. Currently, sixteen subtypes of HA (H1-H16) and nine NA (N1-N9) antigenic variants are known in influenza A virus. Only some of the influenza A subtypes (i.e. H1N1, H1N2 and H3N2) circulate among people, but all combinations of the 16 HA and 9 NA subtypes have been identified in animals, in particular in avian species. Animals infected with influenza A often act as a reservoir for the influenza viruses and certain subtypes have been shown to cross the species barrier to humans, such as the highly pathogenic influenza A strain H5N1.

The influenza type B virus strains are only known to infect humans and seals. Comparison of the sequence divergence among genes of viruses belonging to type A, B, and C virus suggests that, in man, type B viruses evolve slower than type A viruses and faster than type C viruses. It appears that type B viruses mutate at a rate that is two- to three times lower than type A. Two genetically and antigenically distinct lineages of influenza B virus are circulating in humans, as represented by the B/Yamagata/16/88 (also referred to as B/Yamagata) and B/Victoria/2/87 (B/Victoria). Although the spectrum of disease caused by influenza B viruses is generally milder than that caused by influenza A viruses, severe illness requiring hospitalization is still frequently observed with influenza B infection.

Current approaches to dealing with annual influenza epidemics include annual vaccination. However, because circulating influenza viruses in humans are subject to frequent antigenic changes, annual adaptation of the influenza vaccine formulation is required to ensure the closest possible match between the influenza vaccine strains and the circulating influenza strains. In addition, antiviral drugs, such as oseltamivir (Tamiflu®) are used for prevention and treatment of influenza infection. The number of influenza virus strains showing resistance against antiviral drugs, such as oseltamivir is, however, increasing.

An alternative approach is the development of antibody-based prophylactic or therapeutic treatments to neutralize various seasonal and pandemic influenza viruses. Thus, several antibodies capable of neutralizing influenza A and/or B viruses have been described (e.g. WO2008/028946 and WO2013/007770).

In view of the severity of the respiratory illness caused by influenza viruses, as well has the high economic impact of the seasonal epidemics, and the continuing risk for pandemics, there is an ongoing need for new effective means for the prevention and treatment of influenza infections.

SUMMARY OF THE INVENTION

The present invention provides human antibodies, and antigen-binding fragments thereof, capable of specifically binding to neuraminidase of influenza viruses and capable of neutralizing said viruses.

The invention also pertains to nucleic acid molecules encoding the human antibodies, and/or at least the binding region of the human antibodies.

The invention further relates to the use of the antibodies, antigen-binding fragments, and/or the nucleic acid molecules of the invention in the diagnosis, prophylaxis and/or treatment of a subject having, or at risk of developing, an influenza virus infection.

DESCRIPTION OF THE FIGURES

FIG. 1 shows the ADCC activity of anti NA-mAbs. RLU indicates relative luminescence units. Symbols represent observed values and the dotted line the model-predicted dose-response curve. Graphs of a single experiment are shown. CRJB was used as a non-specific isotype matched control IgG (Marissen et al., J Virol 79(8):4672-8, 2005).

DESCRIPTION OF THE INVENTION

Definitions of terms as used in the present invention are given below.

The term "included" or "including" as used herein is deemed to be followed by the words "without limitation".

As used herein the term "antibody" refers to an intact immunoglobulin including monoclonal antibodies, or to an antigen-binding and/or variable domain comprising fragment of an immunoglobulin that competes with the intact immunoglobulin for specific binding to the binding partner of the immunoglobulin, i.e. NA. Regardless of structure, the antigen-binding fragment binds with the same antigen that is recognized by the intact immunoglobulin. An antigen-binding fragment can comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the binding molecule. The term "antibody", as used herein includes all immunoglobulin classes and subclasses known in the art. Depending on the amino acid sequence of the constant domain of their heavy chains, antibodies can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

The term "monoclonal antibody" as used herein refers to a preparation of antibody molecules of single specificity. A monoclonal antibody displays a single binding specificity and affinity for a particular epitope. Accordingly, the term "human monoclonal antibody" refers to an antibody displaying a single binding specificity which has variable and constant regions derived from or based on human germline immunoglobulin sequences or derived from completely synthetic sequences. The method of preparing the monoclonal antibody is not relevant for the binding specificity.

Antigen-binding fragments include, inter alia, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, Edited by: E. Harlow and D, Lane (1988), Cold Spring Harbor Laboratory, Cold Spring Harbor, N.Y.

The term "complementarity determining regions" (CDR) as used herein means sequences within the variable regions of antibodies that usually contribute to a large extent to the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of posttranslational modifications of proteins.

The term "expression-regulating nucleic acid sequence" as used herein refers to polynucleotide sequences necessary for and/or affecting the expression of an operably linked coding sequence in a particular host organism. The expression-regulating nucleic acid sequences, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either homologous or heterologous to the host organism. The identification and employment of expression-regulating sequences is routine to the person skilled in the art.

The term "influenza virus subtype" as used herein in relation to influenza A viruses refers to influenza A virus variants that are characterized by various combinations of the hemagglutinin (H) and neuraminidase (N) viral surface proteins. According to the present invention influenza virus subtypes may be referred to by their H number, such as for example "influenza virus comprising HA of the H1 or H5 subtype", or "H1 influenza virus" "H5 influenza virus", or by referring to their N number, such as for example "influenza virus comprising NA of the N1 or N2 subtype", or by a combination of a H number and an N number, such as for example "influenza virus subtype "H5N1 or H3N2". The term influenza virus "subtype" specifically includes all individual influenza virus "strains" within each subtype, which usually result from mutations and show different pathogenic profiles. Such strains may also be referred to as various "isolates" of a viral subtype. Accordingly, as used herein, the terms "strains" and "isolates" may be used interchangeably. The current nomenclature for human influenza virus strains or isolates includes the geographical location of the first isolation, strain number and year of isolation, usually with the antigenic description of HA and NA given in brackets, e.g. A/Moscow/10/00 (H3N2). Non-human strains also include the host of origin in the nomenclature.

The term "host", as used herein, is intended to refer to an organism or a cell into which a vector such as a cloning vector or an expression vector has been introduced. The organism or cell can be prokaryotic or eukaryotic. Preferably, the hosts isolated host cells, e.g. host cells in culture. The term "host cells" merely signifies that the cells are modified for the (over)-expression of the antibodies of the invention and include B-cells that originally express these antibodies and which cells have been modified to overexpress the binding molecule by immortalization, amplification, enhancement of expression etc.

The term "nucleic acid molecule" as used in the present invention refers to a polymeric form of nucleotides and includes both sense and anti-sense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridisation probes and PCR primers.

The term "operably linked" refers to two or more nucleic acid sequence elements that are usually physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter.

By "pharmaceutically acceptable excipient" is meant any inert substance that is combined with an active molecule such as a drug, agent, or antibody for preparing an agreeable or convenient dosage form. The "pharmaceutically acceptable excipient" is an excipient that is non-toxic to recipients at the used dosages and concentrations, and is compatible with other ingredients of the formulation comprising the drug, agent or binding molecule. Pharmaceutically acceptable excipients are widely applied and known in the art.

The term "specifically binding", as used herein, in reference to the interaction of an antibody, and its binding partner, e.g. an antigen, means that the interaction is dependent upon the presence of a particular structure, e.g. an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the term "specifically binding" means immunospecifically binding to an antigenic determinant or epitope and not immunospecifically binding to other antigenic determinants or epitopes. An antibody that immunospecifically binds to an antigen may bind to other peptides or polypeptides with lower affinity as determined by, e.g., radioimmunoassays (RIA), enzyme-linked immunosorbent assays (ELISA), BIACORE, or other assays known in the art. Antibodies or fragments thereof that immunospecifically bind to an antigen may be cross-reactive with related antigens, carrying the same epitope. Preferably, antibodies or fragments thereof that immunospecifically bind to an antigen do not cross-react with other antigens.

The term "neutralizing" as used herein in relation to the antibodies of the invention refers to antibodies that inhibit an influenza virus from replication, in vitro and/or in vivo, regardless of the mechanism by which neutralization is achieved, or assay that is used to measure the neutralization activity.

The term "therapeutically effective amount" refers to an amount of the antibodies as defined herein that is effective for preventing, ameliorating and/or treating a condition resulting from infection with an influenza A virus. Amelioration as used in herein may refer to the reduction of visible or perceptible disease symptoms, viremia, or any other measurable manifestation of influenza infection.

The term "treatment" refers to therapeutic treatment as well as prophylactic or preventative measures to cure or halt or at least retard disease progress. Those in need of treatment include those already inflicted with a condition resulting from infection with influenza virus as well as those in which infection with influenza virus is to be prevented. Subjects partially or totally recovered from infection with influenza virus might also be in need of treatment. Prevention encompasses inhibiting or reducing the spread of influenza virus or inhibiting or reducing the onset, development or progression of one or more of the symptoms associated with infection with influenza virus.

The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector", as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

DETAILED DESCRIPTION

One of the main targets for influenza neutralizing antibodies is the surface glycoprotein hemagglutinin (HA). Thus, several neutralizing antibodies binding to conserved epitopes in the stem of HA, and capable of broadly neutralizing several influenza virus subtypes have been described in the art, such as e.g. CR6261 (WO2008/028946) and CR9114 (WO2013/007770).

Neuraminidase (NA) is another major glycoprotein on the surface of influenza viruses. The primary function of influenza NA is cleaving of the sialic acid receptors to facilitate the release of viral particles from infected cells. In contrast to HA antibodies, NA antibodies are not known to inhibit the viral infectivity, but they have been shown to reduce viral yield by inhibiting NA enzymatic activity, thus contributing to protection against influenza infection.

In a first aspect the present invention provides neuraminidase (NA)-binding antibodies, and/or antigen-binding fragments thereof, that are capable of neutralizing influenza viruses. The influenza virus strains may be both human and non-human influenza virus strains (i.e. obtained from non-human animals, e.g. birds).

In certain embodiments, the antibodies and antigen-binding fragments are capable of neutralizing at least one influenza A virus strain comprising NA of the N1 subtype.

In certain embodiments, the antibodies and antigen-binding fragments are capable of neutralizing at least one influenza A virus strain comprising NA of the N1 and at least one influenza virus strain comprising NA of the N2 subtype.

Antibodies that bind to influenza NA and are capable of neutralizing influenza viruses, i.e. inhibiting viral replication, are known in the art. At least some of the antibodies of the present invention are unique in that they bind to a different epitope on NA than known NA-antibodies. At least some of the antibodies of the invention are unique in that they have a broader N1 neutralization activity (i.e. are capable of neutralizing at least two, three, four, five or more influenza virus strains comprising NA of the N1 subtype) than known NA-antibodies. At least some of the antibodies of the invention are unique in that they have higher neutralization potency than known NA-antibodies. At least some of the antibodies of the invention are unique in that they neutralize influenza viruses with a distinct mechanism of action, as compared to known NA antibodies.

At least some of the antibodies have neuraminidase-inhibiting activity. In certain embodiments, the antibodies have neuraminidase-inhibiting activity against at least one influenza A virus strain comprising NA of the N1 subtype. In certain embodiments, the antibodies have neuraminidase-inhibiting activity against at least one influenza A virus strain comprising NA of the N1 subtype and at least one influenza virus strain comprising NA of the N2 subtype.

At least some of the antibodies of the invention do not have neuraminidase-inhibiting activity.

The antibodies or antigen-binding fragments of the invention can be used in non-isolated or isolated form. Furthermore, the antibodies or antigen-binding fragments of the invention can be used alone or in a mixture comprising at least one antibodies or antigen-binding fragments) of the invention, and/or with other antibodies or antigen-binding fragments that bind to influenza and have influenza virus inhibiting effect. In other words, the binding molecules can be used in combination, e.g., as a pharmaceutical composition comprising two or more antibodies or antigen-binding fragments of the invention. For example, antibodies or antigen-binding fragments having different, but complementary activities can be combined in a single therapy to achieve a desired prophylactic, therapeutic or diagnostic effect. Optionally, the mixture further comprises at least one other therapeutic agent. Preferably, the therapeutic agent such as, e.g., M2 inhibitors (e.g., amantidine, rimantadine) and/or neuraminidase inhibitors (e.g., zanamivir, oseltamivir) is useful in the prophylaxis and/or treatment of an influenza virus infection.

Typically, antibodies or antigen-binding fragments according to the invention can bind to their binding partners, i.e. an influenza A comprising NA of the N1 subtype (such as H1N1) and/or an influenza A virus comprising NA of the N2 subtype (such as H3N2), and/or fragments thereof, with an affinity constant ($K_d$-value) that is lower than $0.2 \times 10^{-4}$ M, $1.0 \times 10^{-5}$ M, $1.0 \times 10^{-6}$ M, $1.0 \times 10^{-7}$ M, preferably lower than $1.0 \times 10^{-8}$ M, more preferably lower than $1.0 \times 10^{-9}$ M, more preferably lower than $1.0 \times 10^{-10}$ M, even more preferably lower than $1.0 \times 10^{-11}$ M, and in particular lower than $1.0 \times 10^{-12}$ M. The affinity constants can vary for antibody isotypes. For example, affinity binding for an IgM isotype refers to a binding affinity of at least about $1.0 \times 10^{-7}$ M. Affinity constants can for instance be measured using surface plasmon resonance, for example using the BIACORE system (Pharmacia Biosensor AB, Uppsala, Sweden).

The antibodies or antigen-binding fragments of the invention exhibit neutralizing activity. Neutralizing activity can for instance be measured as described herein. Alternative assays measuring neutralizing activity are described in for instance WHO Manual on Animal Influenza Diagnosis and Surveillance, Geneva: World Health Organisation, 2005, version 2002.5. Typically, the antibodies or antigen-binding fragments according to the invention have a neutralizing activity of 50 µg/ml or less, preferably 20 µg/ml or less, more preferably a neutralizing activity of 10 µg/ml or less, even more preferably 5 µg/ml or less, more preferably less than 1 µg/ml, even more preferably less that 0.1 µg/ml, as determined in an in vitro virus neutralization assay (VNA), e.g. as described in Example 3.

The antibodies or antigen-binding fragments according to the invention may bind to influenza virus or a fragment thereof in soluble form such as for instance in a sample or in suspension or may bind to influenza viruses or fragments thereof bound or attached to a carrier or substrate, e.g., microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the antibodies or antigen-binding fragments may bind to influenza virus in purified/isolated or non-purified/non-isolated form.

In certain embodiments, the antibody, or antigen-binding fragment, comprises:
a) a heavy chain CDR1 region of SEQ ID NO:1, a heavy chain CDR2 region of SEQ ID NO:2, and a heavy chain CDR3 region of SEQ ID NO:3,
b) a heavy chain CDR1 region of SEQ ID NO:4, a heavy chain CDR2 region of SEQ ID NO:5, and a heavy chain CDR3 region of SEQ ID NO:6,
c) a heavy chain CDR1 region of SEQ ID NO:7, a heavy chain CDR2 region of SEQ ID NO:8, and a heavy chain CDR3 region of SEQ ID NO:9, or
d) a heavy chain CDR1 region of SEQ ID NO:10, a heavy chain CDR2 region of SEQ ID NO:11, and a heavy chain CDR3 region of SEQ ID NO:12.

In a further embodiment, the antibody, or antigen-binding fragment, comprises:
a) a heavy chain CDR1 region of SEQ ID NO:1, a heavy chain CDR2 region of SEQ ID NO:2, and a heavy chain CDR3 region of SEQ ID NO:3, and a light chain CDR1 region of SEQ ID NO:13, a light chain CDR2 region of SEQ ID NO:14, and a light chain CDR3 region of SEQ ID NO:15;
b) a heavy chain CDR1 region of SEQ ID NO:4, a heavy chain CDR2 region of SEQ ID NO:5, and a heavy chain CDR3 region of SEQ ID NO:6, and a light chain CDR1 region of SEQ ID NO:16, a light chain CDR2 region of SEQ ID NO:17, and a light chain CDR3 region of SEQ ID NO:18;
c) a heavy chain CDR1 region of SEQ ID NO:7, a heavy chain CDR2 region of SEQ ID NO:8, and a heavy chain CDR3 region of SEQ ID NO:9, and a light chain CDR1 region of SEQ ID NO:19, a light chain CDR2 region of SEQ ID NO:20, and a light chain CDR3 region of SEQ ID NO:21; or
d a heavy chain CDR1 region of SEQ ID NO:10, a heavy chain CDR2 region of SEQ ID NO:11, and a heavy chain CDR3 region of SEQ ID NO:12, and a light chain CDR1 region of SEQ ID NO:22, a light chain CDR2 region of SEQ ID NO:23, and a light chain CDR3 region of SEQ ID NO:24. The CDR regions of binding molecules of the invention are shown in Table 5a and b. CDR regions are according to Kabat et al. (1991), as described in Sequences of Proteins of Immunological Interest (U.S. Department of Health and Human Services).

In yet another embodiment, the antibody, or antigen-binding fragment, comprises:
a) a heavy chain variable region of SEQ ID NO: 25,
b) a heavy chain variable region of SEQ ID NO: 27,
c) a heavy chain variable region of SEQ ID NO: 29, or
d) a heavy chain variable region of SEQ ID NO: 31.

In a further embodiment, the antibody or antigen-binding fragment comprises:
a) a heavy chain variable region of SEQ ID NO: 25 and a light chain variable region of SEQ ID NO: 26, b) a binding molecule comprising a heavy chain variable region of SEQ ID NO: 27 and a light chain variable region of SEQ ID NO: 28,
c) a binding molecule comprising a heavy chain variable region of SEQ ID NO: 29 and a light chain variable region of SEQ ID NO: 30,
d) a binding molecule comprising a heavy chain variable region of SEQ ID NO: 31 and a light chain variable region of SEQ ID NO: 32.

The invention further provides immunoconjugates, i.e. molecules comprising at least an antibody and/or antigen-binding fragment as defined herein and further comprising at least one tag, such as inter alia a detectable moiety/agent. Also contemplated in the present invention are mixtures of immunoconjugates according to the invention or mixtures of at least one immunoconjugates according to the invention and another molecule, such as a therapeutic agent or another binding molecule or immunoconjugate. In a further embodiment, the immunoconjugates of the invention may comprise more than one tag. These tags can be the same or distinct from each other and can be joined/conjugated non-covalently to the binding molecules. The tag(s) can also be joined/conjugated directly to the human antibodies and/or antigen-binding fragments through covalent bonding. Alternatively, the tag(s) can be joined/conjugated to the antibodies and/or antigen-binding fragments by means of one or more linking compounds. Techniques for conjugating tags to binding molecules are well known to the skilled artisan.

The tags of the immunoconjugates of the present invention may be therapeutic agents, but they can also be detectable moieties/agents. Tags suitable in therapy and/or prevention may be toxins or functional parts thereof, antibiotics, enzymes, other binding molecules that enhance phagocytosis or immune stimulation. Immunoconjugates comprising a detectable agent can be used diagnostically to, for example, assess if a subject has been infected with an influenza virus or to monitor the development or progression of an influenza virus infection as part of a clinical testing procedure to, e.g., determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the antibodies and/or antigen-binding fragments for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., phagocytosis assays), Western blotting applications, etc. Suitable labels for the detection/analysis/diagnosis techniques and/or methods known in the art are well within the reach of the skilled artisan.

Furthermore, the antibodies and/or antigen-binding fragments and/or immunoconjugates of the invention can also be attached to solid supports, which are particularly useful for in vitro immunoassays or purification of influenza viruses or fragments thereof. Such solid supports might be porous or nonporous, planar or non-planar. The antibodies and/or antigen-binding fragments of the present invention can be fused to marker sequences, such as a peptide to facilitate purification. Examples include, but are not limited to, the hexa-histidine tag, the hemagglutinin (HA) tag, the myc tag or the flag tag. Alternatively, an antibody can be conjugated to a second antibody to form an antibody heteroconjugate. In another aspect the antibodies and/or antigen-binding fragments of the invention may be conjugated/attached to one or more antigens. Preferably, these antigens are antigens which are recognized by the immune system of a subject to which the binding molecule-antigen conjugate is administered. The antigens may be identical, but may also differ from each other. Conjugation methods for attaching the antigens and binding molecules are well known in the art and include, but are not limited to, the use of cross-linking agents.

Next to producing immunoconjugates chemically by conjugating, directly or indirectly, via for instance a linker, the immunoconjugates can be produced as fusion proteins comprising the binding molecules of the invention and a suitable tag. Fusion proteins can be produced by methods known in the art such as, e.g., recombinantly by constructing nucleic acid molecules comprising nucleotide sequences encoding the antibodies and/or antigen-binding fragments in frame with nucleotide sequences encoding the suitable tag(s) and then expressing the nucleic acid molecules.

The invention furthermore provides nucleic acid molecules encoding the antibodies and/or antigen-binding fragments according to the invention. Such nucleic acid molecules can be used as intermediates for cloning purposes, e.g. in the process of affinity maturation as described above. In a preferred embodiment, the nucleic acid molecules are isolated or purified. The skilled man will appreciate that functional variants of these nucleic acid molecules are also intended to be a part of the present invention. Functional variants are nucleic acid sequences that can be directly translated, using the standard genetic code, to provide an amino acid sequence identical to that translated from the parental nucleic acid molecules.

Preferably, the nucleic acid molecules encode the antibodies and/or antigen-binding fragments comprising the CDR regions as described above.

In another embodiment, the nucleic acid molecules encode antibodies and/or antigen-binding fragments comprising a heavy chain comprising a variable region comprising an amino acid sequence as described above. In another embodiment the nucleic acid molecules encode antibodies and/or antigen-binding fragments comprising a light chain comprising a variable region comprising an amino acid sequence as described above.

The invention also provides vectors, i.e. nucleic acid constructs, comprising one or more nucleic acid molecules according to the present invention. Vectors can be derived from plasmids such as inter alia F, R1, RP1, Col, pBR322, TOL, Ti, etc; cosmids; phages such as lambda, lambdoid, M13, Mu, P1, P22, Qβ, T-even, T-odd, T2, T4, T7, etc; plant viruses. Vectors can be used for cloning and/or for expression of the binding molecules of the invention and might even be used for gene therapy purposes. Vectors comprising one or more nucleic acid molecules according to the invention operably linked to one or more expression-regulating nucleic acid molecules are also covered by the present invention. The choice of the vector is dependent on the recombinant procedures followed and the host used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the human binding molecules as described above operably linked to one or more nucleic acid molecules encoding proteins or peptides that can be used to isolate the human binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject of the present invention. Preferably, the hosts are host cells. Host cells include, but are not limited to, cells of mammalian, plant, insect, fungal or bacterial origin. Bacterial cells include, but are not limited to, cells from Gram-positive bacteria or Gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris*, *Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells, such as Chinese Hamster Ovary (CHO) cells, COS cells, BHK cells, NSO cells or Bowes melanoma cells are preferred in the present invention. Mammalian cells provide expressed proteins with posttranslational modifications that are most similar to natural molecules of mammalian origin. Since the present invention deals with molecules that may have to be administered to humans, a completely human expression system would be particularly preferred. Therefore, even more preferably, the host cells are human cells. Examples of human cells are inter alia HeLa, 911, AT1080, A549, HEK293 and HEK293T cells. In preferred embodiments, the human producer cells comprise at least a functional part of a nucleic acid sequence encoding an adenovirus E1 region in expressible format. In even more preferred embodiments, said host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B.V.). For the purposes of this application "PER.C6 cells" refers to cells deposited under number 96022940 or ancestors, passages up-stream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403 the disclosure of which is incorporated herein by reference in its entirety.

Furthermore, the present invention pertains to pharmaceutical compositions comprising at least one antibody and/or antigen-binding fragment of the invention, at least an immunoconjugate, and/or at least one nucleic acid molecule according to the invention, or combinations thereof. The pharmaceutical composition of the invention further comprises at least one pharmaceutically acceptable excipient. Pharmaceutically acceptable excipients are well known to the skilled person. The pharmaceutical composition according to the invention may further comprise at least one other therapeutic agent. Suitable agents are also well known to the skilled artisan.

In a preferred embodiment the pharmaceutical composition according to the invention comprises at least one additional antibody or antigen-binding fragment thereof, i.e. the pharmaceutical composition can be a cocktail or mixture of antibodies. The pharmaceutical composition may comprise at least two antibodies or antigen-binding fragments thereof according to the invention, or at least one antibody or antigen-binding fragment thereof according to the invention and at least one further influenza virus binding and/or neutralizing molecule, such as another antibody directed against the HA protein or against other antigenic structures present on influenza viruses, such as M2. A pharmaceutical composition according to the invention can further comprise at least one other therapeutic, prophylactic and/or diagnostic agent. Preferably, the pharmaceutical composition comprises at least one other prophylactic and/or therapeutic agent. Preferably, said further therapeutic and/or prophylactic agents are agents capable of preventing and/or treating an influenza virus infection and/or a condition resulting from such an infection. Therapeutic and/or prophylactic agents include, but are not limited to, anti-viral agents. Such agents can be binding molecules, small molecules, organic or inorganic compounds, enzymes, polynucleotide sequences, anti-viral peptides, etc. Other agents that are currently used to treat patients infected with influenza viruses are M2 inhibitors (e.g., amantidine, rimantadine) and/or neuraminidase inhibitors (e.g., zanamivir, oseltamivir). These can be used in combination with the binding molecules of the invention. "In combination" herein means simultaneously, as separate formulations, or as one single combined formulation, or according to a sequential administration regimen as separate formulations, in any order. Agents capable of preventing and/or treating an infection with influenza virus and/or a condition resulting from such an infection that are in the experimental phase might also be used as other therapeutic and/or prophylactic agents useful in the present invention.

The antibodies or pharmaceutical compositions of the invention can be tested in suitable animal model systems prior to use in humans. Such animal model systems include, but are not limited to, mouse, ferret and monkey.

The choice of the optimal route of administration of the antibodies and/or pharmaceutical compositions will be influenced by several factors including the physicochemical properties of the active molecules within the compositions, the urgency of the clinical situation and the relationship of the plasma concentrations of the active molecules to the desired therapeutic effect. The preferred administration route is intravenous or by inhalation.

In a further aspect, the antibodies or antigen-binding fragments thereof, immunoconjugates, nucleic acid molecules and/or pharmaceutical compositions of the invention are for use as a medicament, preferably for use in the diagnosis, prophylaxis and/or treatment of influenza infection. In addition, a method of diagnosis, treatment and/or prevention of an influenza virus infection using at least one antibody, or antigen-binding fragment thereof, nucleic acid molecule, immunoconjugate and/or pharmaceutical compositions of the invention is another part of the present invention. The above-mentioned molecules can inter alia be used in the diagnosis, prophylaxis, treatment, or combination thereof, of an influenza virus infection caused influenza viruses comprising NA of the N1 and/or N2 subtype. The above-mentioned molecules or compositions may be employed in conjunction with other molecules useful in diagnosis, prophylaxis and/or treatment. For instance, the antibodies, fragments, immunoconjugates, or pharmaceutical compositions of the invention can be co-administered with a vaccine against influenza virus (if available). Alternatively, the vaccine may also be administered before or after administration of the antibodies of the invention.

The prophylaxis and/or treatment may be targeted at patient groups that are susceptible to influenza infection. Such patient groups include, but are not limited to e.g., the elderly (e.g. ≥50 years old, ≥60 years old, and preferably ≥65 years old), the young (e.g. ≤5 years old, ≤1 year old), hospitalized patients and already infected patients who have been treated with an antiviral compound but have shown an inadequate antiviral response.

Dosage regimens can be adjusted to provide the optimum desired response (e.g., a therapeutic response). A suitable dosage range may for instance be 0.01-100 mg/kg body weight, preferably 0.1-50 mg/kg body weight, preferably 0.01-15 mg/kg body weight. Furthermore, for example, a single bolus may be administered, several divided doses may be administered over time or the dose may be proportionally reduced or increased as indicated by the exigencies of the therapeutic situation. The exact dosing regimen is usually sorted out during clinical trials in human patients.

In another aspect, the invention concerns the use of an antibody, or antigen-binding fragment thereof, immunoconjugate, nucleic acid molecule, and/or pharmaceutical composition according to the invention in the preparation of a medicament for the diagnosis, prophylaxis, treatment, or combination thereof, of an influenza virus infection, in particular an influenza virus infection caused influenza viruses comprising NA of the N1 and/or N2 subtype.

Next to that, kits comprising at least one antibody or antigen-binding fragment thereof, at least one immunoconjugate, and/or at least one nucleic acid molecule, or a combination thereof are also a part of the present invention. Optionally, the above-described components of the kits of the invention are packed in suitable containers and labelled for diagnosis, prophylaxis and/or treatment of the indicated conditions. The above-mentioned components may be stored in unit or multi-dose containers as an aqueous, preferably sterile, solution or as a lyophilised, preferably sterile, formulation for reconstitution. The containers may be formed from a variety of materials such as glass or plastic and may have a sterile access port (for example, the container may be an intravenous solution bag or a vial having a stopper pierceable by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products, that contain information about for example the indications, usage, dosage, manufacture, administration, contraindications and/or warnings concerning the use of such therapeutic, prophylactic or diagnostic products.

The antibodies or antigen-binding fragments according to the present invention can also be advantageously used as a diagnostic agent in an in vitro method for the detection of influenza virus. The invention thus further pertains to a method of detecting influenza virus in a sample, wherein the method comprises the steps of (a) contacting a sample with a diagnostically effective amount of an antibody or antigen-binding fragment thereof or an immunoconjugate according to the invention, and (b) determining whether the antibody or antigen-binding fragment thereof or immunoconjugate specifically binds to a molecule of the sample. The sample may be a biological sample including, but not limited to blood, serum, stool, sputum, nasophargyal aspirates, bronchial lavages, urine, tissue or other biological material from (potentially) infected subjects, or a non-biological sample such as water, drink, etc. The (potentially) infected subjects may be human subjects, but also animals that are suspected as carriers of influenza virus might be tested for the presence of the virus using the human antibodies or antigen-binding fragments thereof or immunoconjugates of the invention. The sample may first be manipulated to make it more suitable for the method of detection. Manipulation means inter alia treating the sample suspected to contain and/or containing the virus in such a way that the virus will disintegrate into antigenic components such as proteins, (poly)peptides or other antigenic fragments. Preferably, the human antibodies or antigen-binding fragments thereof or immunoconjugates of the invention are contacted with the sample under conditions which allow the formation of an immunological complex between the human antibodies or antigen-binding fragments thereof and the virus or antigenic components thereof that may be present in the sample. The formation of an immunological complex, if any, indicating the presence of the virus in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, BIACORE and Western blot analyses.

Preferred assay techniques, especially for large-scale clinical screening of patient sera and blood and blood-derived products are ELISA and Western blot techniques. ELISA tests are particularly preferred. For use as reagents in these assays, the human antibodies or antigen-binding fragments thereof or immunoconjugates of the invention are conveniently bonded to the inside surface of microtiter wells. The human antibodies or antigen-binding fragments thereof or immunoconjugates of the invention may be directly bonded to the microtiter well.

Furthermore, human antibodies or antigen-binding fragments thereof of the invention can be used to identify specific binding structures of influenza virus. The binding structures can be epitopes on proteins and/or polypeptides. They can be linear, but also structural and/or conformational. In one embodiment, the binding structures can be analysed by means of PEPSCAN analysis (see inter alia WO 84/03564, WO 93/09872). Alternatively, a random peptide library comprising peptides from a protein of influenza virus can be screened for peptides capable of binding to the human antibodies or antigen-binding fragments thereof of the invention.

The invention is further illustrated in the following examples and figures. The examples are not intended to limit the scope of the invention in any way.

EXAMPLES

Example 1: FACS-Based Binding Assay

Binding features of the anti-NA antibodies were assessed by testing their reactivity to NA-expressing cells by flow cytometry. FreeStyle™ 293-F cells (Invitrogen™) were transfected with plasmid containing a NA-encoding gene of choice using 293Fectin™ (Invitrogen™). Constructs containing the NA gene from the following viruses were used: H1N1 A/California/07/2009, H1N1 A/Brisbane/59/2007, H1N1 A/Puerto Rico/8/1934, H5N1 A/Hong Kong/156/1997, H5N1 A/Vietnam/1194/2004 (NIBRG-14), H3N2 A/Perth/16/2009 and H3N2 A/Hong Kong/1/1968.

For a 30 ml transfection suspension, 30 µg of plasmid DNA and 40 µl of 293Fectin™ were separately diluted in Opti-MEM® I (Gibco®) to a total volume of 1 ml. After 5 min incubation, the diluted DNA was added to the diluted 293Fectin™ to obtain a total volume of 2 ml that was incubated for 20-30 min at room temperature to allow the DNA-293Fectin™ complexes to form. Two ml of DNA-293Fectin™ complex were added to 28 ml cell suspension containing $3\times10^7$ cells to obtain a total volume of 30 ml (final cell density: $1\times10^6$ cells/ml). To the negative control, 2 ml of Opti-MEM® I instead of DNA-293Fectin™ complex were added. Cells were incubated on an orbital shaker rotating at 125 rpm for 48 h at 37° C., 8% CO2.

After 48 h, approximately $2\times10^5$ cells were plated in a 96-well U-bottom plate and washed two times with PBS-1% BSA by resuspending and centrifuging the cells 3 min at 300×g. Subsequently, 100 µl of serial 10-fold dilutions of IgGs (5-0.005 µg/ml) were added to cells and incubated for 1 h at 4° C., after which cells were washed two times with PBS-1% BSA. Bound IgGs were detected by first incubating cells with goat F(ab')2 anti-human IgG (Southern Biotech) for 30 min at 4° C. After that, cells were washed three times with PBS-1% BSA by resuspending and centrifuging cells for 3 min at 300×g, and a final resuspension in 200 µl PBS-1% BSA, before being sorted using a BD FACS Canto II.

In this assay, all anti-NA antibodies bound to the different NAs of the N1 subtype, while CR12042 and to a lesser extend CR12044 additionally recognized one of the two tested NAs of subtype N2 (Table 1). NA-expressing cells were stained with anti-NA IgG and analyzed by flow cytometry to assess percentage of stained cells and thus relative binding. The table shows binding results for tested IgG at 5 µg/ml except for CR12041, where results refer to an IgG concentration of 0.5 µg/ml (higher concentrations showed nonspecific binding to non-transfected cells used as negative control).Relative binding is given as –: no binding; +: 25-50% binding; ++: 50-75% binding; +++: 75-100% binding.

Example 2: Neuraminidase Inhibition Assay

The ability of anti-NA antibodies of the invention to inhibit neuraminidase activity of influenza viruses was assessed using the NA-XTD™ Influenza Neuraminidase Assay Kit (Applied Biosystems/Life Technologies) following the manufacturer's specifications with minor adjustments. For each influenza strain, serial dilutions of the virus stock were tested to determine the virus dilution resulting in a chemoluminescent signal of $10^5$ RLU. Antibodies were serially four-fold diluted (100-0.00004 µg/ml) in NA-XTD™ assay buffer containing 0.1% asialofetuin (Sigma Aldrich). From each dilution, 25 µl was transferred to a NA-Star™ Detection Microplate and mixed with 25 µl diluted virus. The plate was incubated at 37° C., 10% $CO_2$ for 20 min before adding 25 µL/well of the NA-XTD™ Substrate (diluted in NA-XTD™ assay buffer containing 0.1% asialofetuin). Subsequently, the plate was incubated at room temperature and in the dark for 20-30 min, after which 60µl NA-XTD™ Accelerator solution was added to each well. The plate was incubated for 3 min at room temperature and in the dark before the luminescent signal was read using a Synergy Neo Reader (BioTek). In each experimental session, oseltamivir (Roche) was used as positive control of NA activity inhibition. Results were transformed using the square root transformation to stabilize the variances over the curve. Curve fitting was performed applying a four-parameter logistic (4-PL) nonlinear regression model and $EC_{50}$ values were determined for all curves with a negative slop factor.

The ability of anti-NA antibodies to inhibit neuraminidase activity of influenza viruses was assessed for the H1N1 strains A/New Caledonia/20/1999, A/Mississippi/3/2001, A/Mississippi/3/2001 H274Y (an oseltamivir-resistant mutant with a H274Y mutation in NA), A/Brisbane/59/2007; H5N1 strain A/Hong Kong/156/1997 (reverse genetic reassortant); the H3N2 strains A/Wisconsin/67/2005, A/Brisbane/10/2007 and A/Perth/16/2009. The murine anti-NA mAb 2B9 was used as comparator since it was shown to inhibit the enzymatic activity of NA from H5N1 and of selected H1N1 strains (Shoji et al. Human Vaccines 7:suppl. 199-204, 2011). The active metabolite oseltamivir carboxylate of the NA inhibitor oseltamivir was used as positive control for neuraminidase inhibition.

Results obtained show that CR12042 and CR12044 have a broader NA inhibition activity than the comparator mAb 2B9. Moreover, CR12042 displays higher potency than 2B9 in inhibiting NA activity of the H5N1 strain A/Hong Kong/156/1997, when tested in the same assay. Both CR12042 and CR12044 inhibit the NA enzymatic activity of a H1N1 strain known to be resistant to oseltamivir action (A/Mississippi/3/2001 H274Y). CR12040 and CR12041 did not show NA inhibition activity under the assay conditions tested.

TABLE 1

| Binding characteristics of anti-NA IgGs. | | | | | |
|---|---|---|---|---|---|
| Virus | | CR12040 | CR12041 | CR12042 | CR12044 |
| H1N1 | A/Puerto Rico/8/1934 | + | + | ++ | +++ |
| H1N1 | A/Brisbane/59/2007 | +++ | +++ | +++ | +++ |
| H1N1 | A/California/07/2009 | ++ | +++ | +++ | +++ |
| H5N1 | A/Hong Kong/156/1997 | ++ | +++ | +++ | ++ |
| H5N1 | A/Vietnam/1194/2004 (NIBRG-14) | +++ | +++ | +++ | +++ |
| H3N2 | A/Perth/16/2009 | – | – | ++ | + |
| H3N2 | A/Hong Kong/1/1968 | – | – | – | – |

TABLE 2

Neuraminidase inhibition activity of anti-NA IgGs. EC50 values are reported
and expressed in μg/ml except for oseltamivir where they are expressed in μM.

| | Virus | CR12040 | CR12041 | CR12042 | CR12044 | 2B9 | Oseltamivir |
|---|---|---|---|---|---|---|---|
| H1N1 | A/New Caledonia/20/1999 | >100 | >100 | 0.18 | 0.17 | >270 | 0.47 |
| H1N1 | A/Brisbane/59/2007 | >100 | >100 | 0.11 | 0.17 | >270 | 0.29 |
| H1N1 | A/Mississippi/3/01 | >100 | >100 | 0.12 | 0.96 | >270 | 0.46 |
| H1N1 | A/Mississippi/3/01 H274Y | >100 | >100 | 0.15 | 3.05 | >270 | 123.4 |
| H5N1 | A/Hong Kong/156/1997 | >100 | >100 | 0.02 | 7.23 | 0.16 | 0.38 |
| H3N2 | A/Wisconsin/67/2005* | N.D. | N.D. | 1.87 | N.D. | >200 | 0.31 |
| H3N2 | A/Brisbane/10/2007* | N.D. | N.D. | 4.80 | N.D. | >200 | 0.30 |
| H3N2 | A/Perth/16/2009 | N.D. | N.D. | 5.01 | N.D. | >200* | 0.64 |

Values represent the geomean of two separate experiments except for *where only one experiment was performed. N.D.: not determined, IgG were not tested. A ">" indicates that no $EC_{50}$ could be determined for a dilution series with the indicated maximum concentration of agent tested.

Example 3: Virus Neutralization Assay

To determine whether the anti-NA antibodies are capable of neutralizing H1N1 and H5N1 infection in vitro, virus neutralization assays (VNA) were performed with the following H1N1 viruses: A/New Caledonia/20/1999, A/Mississippi/3/2001, A/Mississippi/3/2001 274Y (oseltamivir resistant, H274Y mutation in NA), A/California/07/2009 and the H5N1 viruses A/Hong Kong/156/1997 and A/Vietnam/1194/2004 (NIBRG-14); and the H3N2 viruses A/Wisconsin/67/2005, A/Brisbane/10/2007, A/Perth/16/2009. To this end, 96-well plates were coated with $4 \times 10^4$ MDCK-SIAT1 cells (Sigma Aldrich) per well in infection medium containing 3 μg/ml trypsin. Antibodies, including controls, were two-fold serially diluted in plain medium containing L-glutamine, in a 96-well plate. The virus was diluted to a titer of $5.7 \times 10^3$ $TCID_{50}$/ml with double infection medium (plain medium+L-glutamine containing 6 μg/ml trypsin) and added at a 1:1 ratio to the antibody-dilution containing plate, resulting in a final amount of $2.85 \times 10^3$ $TCID_{50}$/ml of virus. The plate was subsequently incubated for 1.5-2 h at 37° C., 10% $CO_2$ before infecting 100 μl/well MDCK cells by adding 35 μl antibody-virus mix containing 100 $TCID_{50}$ of virus. Plates were then incubated for three days at 37° C., 10% $CO_2$. After three days, the assay was analyzed by HAU read out after mixing 50 μl of virus sample with 50 μl 1% turkey red blood cell (TRBC) solution in PBS in a 96-well plate. After 60 min (±30 min), hemagglutination was visually scored. Titers were calculated using the Spearman-Karber method and expressed in IC50 for virus neutralization assays.

endpoint titer (log 10)=$X_0-(d/2)+(d/n)*\Sigma X_i$ with:

$X0$=the $\log_{10}$ value of the highest dilution at which all inoculations are still positive d=the $\log_{10}$ value of the dilution factor n=the number of replicates at each dilution $\Sigma X_i$=the sum of all wells that are positive including and after dilution $X_0$ As shown in Table 3, CR12042 and CR12044 neutralize all viruses tested except for A/Hong Kong/156/1997 that was not neutralized by CR12044. CR12041 inhibits the infection of three out of four H1N1 strains (including an oseltamivir resistant virus), despite the absence of any NA inhibition activity. No neutralization activity was observed for CR12040.

TABLE 3

Neutralization activity of anti-NA IgGs. Titers were calculated using the Spearman-Kärber
method and expressed as $IC_{50}$ in μg/ml for the mAbs, and in μM for oseltamivir carboxylate.

| Virus | | CR12040 | CR12041 | CR12042 | CR12044 | Oseltamivir |
|---|---|---|---|---|---|---|
| H1N1 | A/New Caledonia/20/1999 | >50 | 0.74 | 0.20 | 0.13 | 0.02 |
| H1N1 | A/California/07/2009 (NYMC X-181) | >50 | >50 | 0.26 | 0.41 | 0.08 |
| H1N1 | A/Mississippi/3/2001 | >50 | 0.59 | 0.20 | 0.37 | 0.01 |
| H1N1 | A/Mississippi/3/2001 H274Y | >50 | 0.45 | 0.48 | 1.25 | >5 |
| H5N1 | A/Hong Kong/156/1997 | >50 | >50 | 0.29 | >50 | 0.08 |
| H5N1 | A/Vietnam/1194/2004 (NIBRG14) | >50 | >50 | 5.45 | 0.74 | 0.08 |
| H3N2 | A/Wisconsin/67/2005 | N.D. | N.D. | >100* | N.D. | N.D. |
| H3N2 | A/Brisbane/10/2007 | N.D. | N.D. | >100* | N.D. | N.D. |
| H3N2 | A/Perth/16/2009 | N.D. | N.D. | >100* | N.D. | N.D. |

Values represent the geomean of two separate experiments except for * where only one experiment was performed.

N.D.: not determined, IgG were not tested.

>50 and >100 indicate no titers could be determined at the maximum amount tested, which were 50 and 100 μg/ml, respectively.

Example 4: ADCC Reporter Assay

The ability of anti-NA antibodies to engage the human FcγRIIIa receptor was measured using an ADCC Reporter Bioassay (Promega). Target A549 cells were infected with H1N1 strains A/New Caledonia/20/1999, A/Mississippi/3/2001, A/Mississippi/3/2001 274Y (oseltamivir resistant), A/Brisbane/59/2007; or H5N1 strains A/Vietnam/1194/2004 (NIBRG-14), A/Hong Kong/156/1997. After 24 hours, cells were seeded into white 96-wells plates and incubated with serial dilutions of each anti-NA IgG. Jurkat effector T-cells (stably transfected with FcγRIIIa V158 and NFAT-RE Luciferase) were added to the target cells and incubated for 6 hours. Bio-Glo Luciferase Assay Substrate solution (Promega) was added to the wells and luminescence (in RLUs) was measured with a Wallac Microbeta 1450 luminescence counter (TriLux). RLU data were fitted using a four-parameter logistic (4-PL) curve fit, using a transform both sides approach (Findley et al., 2007; Aaps J, 2007. 9(2): p. E260-7) with a $\log_{10}$ transformation. For each plate, the estimation of the lower asymptote was stabilized by using responses without mAb as an anchor. Parameter estimates for the upper asymptote (D), slope factor (B), and $EC_{50}$ (C) were sample-dependent with a shared lower asymptote (A) per plate. Hook effects (decreasing RLU after reaching maximum signal) were addressed with down-weighing to reduce impact on curve fit.

Ability of anti-NA IgGs to engage the human FcγRIIIa receptor was measured by an ADCC Reporter Bioassay (Promega) using as target A549 cells infected with the H1N1 viruses: A/New Caledonia/20/1999, A/Brisbane/59/2007, A/Mississippi/3/2001, A/Mississippi/3/2001 274Y (oseltamivir resistant) and the H5N1 viruses: A/Hong Kong/156/1997 (reverse genetic reassortant) and A/Vietnam/1194/2004 (NIBRG-14), A/Vietnam/1194/2004 (NIBRG-14).

As shown in Table 4, all antibodies tested were able to engage the human FcγRIIIa thus triggering the intracellular pathway leading to the chemoluminescent signal. Responses were dose-dependent and Table 4 lists estimated $EC_{50}$ values for tested viruses, as well as maximum signal induction as expressed in the D/A ratio (with D=maximum asymptote, A=minimum asymptote).

TABLE 4

ADCC activity of anti NA-mAbs. Estimated EC50 values are reported and expressed in μg/ml. Maximum signal induction is as expressed in the D/A ratio (with D = maximum asymptote, A = minimum asymptote).

| | | CR12040 | | CR12041 | | CR12042 | | CR12044 | |
|---|---|---|---|---|---|---|---|---|---|
| | Virus | $EC_{50}$ | D/A | $EC_{50}$ | D/A | $EC_{50}$ | D/A | $EC_{50}$ | D/A |
| H1N1 | A/Brisbane/59/2007 | 3.83 | 2.73 | 1.97 | 2.15 | 0.08 | 6.11 | 0.28 | 6.49 |
| H1N1 | A/New Caledonia/20/1999 | 0.07 | 3.19 | 1.61 | 4.08 | 0.28 | 17.73 | 0.93 | 17.51 |
| H1N1 | A/Mississippi/03/2001 | 0.06 | 9.26 | 0.58 | 8.38 | 0.14 | 17.39 | 5.19 | 20.19 |
| H1N1 | A/Mississippi/03/2001 H274Y | 0.04 | 9.05 | 0.13 | 9.25 | 0.16 | 17.44 | 17.74 | 16.80 |
| H5N1 | A/Hong Kong/156/1997 | 1.22 | 3.10 | 1.09 | 5.48 | 0.01 | 6.87 | 11.57 | 2.37 |
| H5N1 | A/Vietnam/1194/2004 (NIBRG14) | 1.37 | 3.44 | 0.68 | 6.11 | 0.01 | 9.27 | 0.35 | 8.28 |

The sequences of the heavy and light chain variable regions and CDR regions are given below (Table 5a and 5b).

TABLE 5a

Amino acid sequences of heavy chain CDRs

| single chain name | CDR1 (SEQ ID NO) | CDR2 (SEQ ID NO) | CDR3 (SEQ ID NO) |
|---|---|---|---|
| sc12-040 | GYTFTNYY (1) | INPLHGGT (2) | VKERDTTMATDYYGRSGCFDY (3) |
| sc12-041 | GYTFTNYY (4) | INPSSGGT (5) | ARAGEGKSRFGEGKLRYFYYGMDV (6) |
| sc12-042 | GDTFSSYT (7) | IIPIFGTA (8) | ARGPDNHSDRYFYYGMDV (9) |
| sc12-044 | GGAFRTSV (10) | IIPTLDTA (11) | ATDYGGNSDRLGSYSFAFDV (12) |

TABLE 5b

Amino acid sequences of light chain CDRs

| single chain name | CDR1 (SEQ ID NO) | CDR2 (SEQ ID NO) | CDR3 (SEQ ID NO) |
|---|---|---|---|
| sc12-040 | QSVRSY (13) | DAS (14) | QQRSNWPIT (15) |
| sc12-041 | QSLLHSNGYNY (16) | LGS (17) | MQALQTPLT (18) |
| sc12-042 | QSLLHSTGNNY (19) | LGS (20) | MQALQTPRT (21) |
| sc12-044 | SSNIGSNT (22) | SNN (23) | AAWDDSLNGWV (24) |

CR12040:
Heavy chain variable region (SEQ ID NO: 25):
QVQLVQSGAEVKKPGASVKVSCKASGYTFTNYYINWVRQAPGQGLEWMGR

INPLHGGTGFAEKFQGRLTMTRDTSTSTVDMELSSLRSEDTAIYYCVKER

DTTMATDYYGRSGCFDYWGQGTLVTVSS

Light chain variable region (SEQ ID NO: 26):
EIVLTQSPATLSLSPGERATLSCRASQSVRSYLAWYQQKPGQAPRLLIYD

ASNRATGIPARFSGSGSGTDFSLTISSLEPEDFAVYYCQQRSNWPITFGQ

GTRLEIK

CR12041
Heavy chain variable region (SEQ ID NO: 27):
EVQLVQSGAEVKKPGASVKVSCKAA GYTFTNYY LHWVRQAPGQGLESM

GIINPSSGGT IYAQKFQGRVTMTRDTSTSTVFMELSSLTSEDTAVYYC

ARAGEGKSRFGEGKLRYFYYGMDVWGQGTTVTVSS

Light chain variable region (SEQ ID NO: 28):
DVVMTQSPLSLPVTPGEPASISCRSS QSLLHSNGYNYLDWYLQKPGQ

SPQLLIY LGS NRASGVPDRFSGSGSGTDFTLKISRVEAEDVGVYYC

MQALQTPLTFGGGTKLEIK

CR12042
Heavy chain variable region (SEQ ID NO: 29):
EVQLVESGAEVRKPGSSVKVSCTAS GDTFSSYT ITWVRQAPGQGLEWM

GEIIPIFGTA NYAQKFQGRVTLTADESTTTAYMDLSSLRSEDTAVYYC

ARGPDNHSDRYFYYGMDVWGQGTTVTVSS

Light chain variable region (SEQ ID NO: 30):
EIVLTQSPLSLPVTPGEPASISCRSS QSLLHSTGNNY LDWYLQKPGQS

PQLLIYLGS NRASGVPDRFSGSGSGTDFTLKISRVEAEDVGVYYC

MQALQTPRTFGQGTKVDIK

CR12044
Heavy chain variable region (SEQ ID NO: 31):
EVQLVQSGSEVRKPGSTVKVSCKGS GGAFRTSV IHWVRQAPGQGLRWM

GGIIPTLDTA NHAQEFQGRATITADESTTTAYLELSSLRSEDSAVYYC

ATDYGGNSDRLGSYSFAFDVWGQGTTVTVSS

Light chain variable region (SEQ ID NO: 32):
QSVLTQPPSASGTPGQRVTISCSGS SSNIGSNT VNWYQQLPGTAPKLL

IY SNNQRPSGVPDRFSGSKSGTSASLAISGLQSEDEADYYC AAWDDSL

NGWVFGGGTQLTVL

The invention claimed is:

1. An isolated antibody or antigen-binding fragment thereof that specifically binds neuraminidase (NA) of an influenza A virus, wherein the antibody, or antigen binding fragment is selected from the group consisting of:
   a) an antibody, or antigen-binding fragment, comprising a heavy chain CDR1 region of SEQ ID NO: 1, a heavy chain CDR2 region of SEQ ID NO:2, and a heavy chain CDR3 region of SEQ ID NO:3, and a light chain CDR1 region of SEQ ID NO: 13, a light chain CDR2 region of SEQ ID NO: 14, and a light chain CDR3 region of SEQ ID NO: 15;
   b) an antibody or antigen-binding fragment comprising a heavy chain CDR1 region of SEQ ID NO:4, a heavy chain CDR2 region of SEQ ID NO:5, and a heavy chain CDR3 region of SEQ ID NO:6, and a light chain CDR1 region of SEQ ID NO: 16, a light chain CDR2 region of SEQ ID NO: 17, and a light chain CDR3 region of SEQ ID NO: 18;
   c) an antibody or antigen-binding fragment comprising a heavy chain CDR1 region of SEQ ID NO:7, a heavy chain CDR2 region of SEQ ID NO:8, and a heavy chain CDR3 region of SEQ ID NO:9, and a light chain CDR1 region of SEQ ID NO: 19, a light chain CDR2 region of SEQ ID NO:20, and a light chain CDR3 region of SEQ ID NO:21; and
   d) an antibody or antigen-binding fragment comprising a heavy chain CDR1 region of SEQ ID NO: 10, a heavy chain CDR2 region of SEQ ID NO: 11, and a heavy chain CDR3 region of SEQ ID NO: 12, and a light chain CDR1 region of SEQ ID NO:22, a light chain CDR2 region of SEQ ID NO:23, and a light chain CDR3 region of SEQ ID NO:24.

2. The antibody, or antigen-binding fragment thereof, according to claim 1, which is capable of neutralizing at least one influenza A virus strain comprising NA of the N1 subtype.

3. The antibody, or antigen-binding fragment thereof, according to claim 1, wherein the antibody or antigen-binding fragment furthermore is capable of neutralizing at least one influenza A virus strain comprising NA of the N2 subtype.

4. The antibody, or antigen-binding fragment thereof, according to claim 1, wherein the antibody or antigen-binding fragment has neuraminidase inhibiting activity against at least one influenza virus strain comprising NA of the N1 subtype.

5. The antibody, or antigen-binding fragment thereof, according to claim 3, wherein the antibody or antigen-binding fragment has neuraminidase inhibiting activity against at least one influenza virus strain comprising NA of the N1 subtype and at least one influenza virus strain comprising NA of the N2 subtype.

6. The antibody, or antigen-binding fragment thereof, according to claim 1, wherein the antibody or antigen-binding fragment has no neuraminidase inhibiting activity.

7. An isolated antibody or antigen-binding fragment thereof that specifically binds neuraminidase (NA) of an influenza A virus, wherein the antibody or antigen binding fragment is selected from the group consisting of:
   a) an antibody, or antigen-binding fragment, comprising a heavy chain variable fragment of SEQ ID NO: 25; and a light chain variable region of SEQ ID NO: 26;
   b) an antibody, or antigen-binding fragment, comprising a heavy chain variable fragment of SEQ ID NO: 27; and a light chain variable region of SEQ ID NO: 28;
   c) an antibody, or antigen-binding fragment, comprising a heavy chain variable fragment of SEQ ID NO: 29; and a light chain variable region of SEQ ID NO: 30; and
   d) an antibody, or antigen-binding fragment, comprising a heavy chain variable fragment of SEQ ID NO: 31; and a light chain variable region of SEQ ID NO: 32.

8. A nucleic acid molecule encoding the antibody or antigen-binding fragment according to claim 1.

9. An immunoconjugate comprising the antibody or antigen-binding fragment according to claim 1, further comprising a tag.

10. A pharmaceutical composition comprising the immunoconjugate according to claim 9.

11. A pharmaceutical composition comprising the antibody or antigen-binding fragment according to claim 1.

12. A pharmaceutical composition comprising the antibody or antigen-binding fragment according to claim 7.

13. A method of treating or preventing influenza infection in a subject in need thereof, the method comprising administering to the subject the pharmaceutical composition according to claim 10.

14. A method of treating or preventing influenza infection in a subject in need thereof, the method comprising administering to the subject the pharmaceutical composition according to claim 11.

15. A method of treating or preventing influenza infection in a subject in need thereof, the method comprising administering to the subject the pharmaceutical composition according to claim 12.

16. A method of diagnosing influenza infection in a subject, the method comprising contacting a sample from the subject with the antibody or antigen-binding fragment according to claim 1.

17. A method of diagnosing influenza infection in a subject, the method comprising contacting a sample from the subject with the immunoconjugate according to claim 9.

18. A method of diagnosing influenza infection in a subject, the method comprising contacting a sample from the subject with the antibody or antigen-binding fragment according to claim 7.

19. An immunoconjugate comprising the antibody or antigen-binding fragment according to claim 7, further comprising a tag.

20. A pharmaceutical composition comprising the immunoconjugate according to claim 19.

21. A method of diagnosing influenza infection in a subject, the method comprising contacting a sample from the subject with the immunoconjugate according to claim 19.

22. A nucleic acid molecule encoding the antibody or antigen-binding fragment according to claim 7.

* * * * *

SEQUENCE LISTING

<160> NUMBER OF SEQ ID NOS: 32

<210> SEQ ID NO 1
<211> LENGTH: 8
<212> TYPE: PRT
<213> ORGANISM: Artificial Sequence
<220> FEATURE:
<223> OTHER INFORMATION: 12-040 HCDR1

<400> SEQUENCE: 1

Gly Tyr Thr Phe Thr Asn Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: 12-040 HCDR2

<400> SEQUENCE: 2

Ile Asn Pro Leu His Gly Gly Thr
1               5

-continued

```
<210> SEQ ID NO 3
<211> LENGTH: 21
<212> TYPE: PRT
<213> ORGANISM: Artificial Sequence
<220> FEATURE:
<223> OTHER INFORMATION: 12-040 HCDR3

<400> SEQUENCE: 3

Val Lys Glu Arg Asp Thr Thr Met Ala Thr Asp Tyr Tyr Gly Arg Ser
1               5                   10                  15

Gly Cys Phe Asp Tyr
            20

<210> SEQ ID NO 4
<211> LENGTH: 8
<212> TYPE: PRT
<213> ORGANISM: Artificial Sequence
<220> FEATURE:
<223> OTHER INFORMATION: 12-041 HCDR1

<400> SEQUENCE: 4

Gly Tyr Thr Phe Thr Asn Tyr Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: 12-041 HCDR2

<400> SEQUENCE: 5

Ile Asn Pro Ser Ser Gly Gly Thr
1               5

<210> SEQ ID NO 6
<211> LENGTH: 24
<212> TYPE: PRT
<213> ORGANISM: Artificial Sequence
<220> FEATURE:
<223> OTHER INFORMATION: 12-041 HCDR3

<400> SEQUENCE: 6

Ala Arg Ala Gly Glu Gly Lys Ser Arg Phe Gly Glu Gly Lys Leu Arg
1               5                   10                  15

Tyr Phe Tyr Tyr Gly Met Asp Val
            20

<210> SEQ ID NO 7
<211> LENGTH: 8
<212> TYPE: PRT
<213> ORGANISM: Artificial Sequence
<220> FEATURE:
<223> OTHER INFORMATION: 12-042 HCDR1

<400> SEQUENCE: 7

Gly Asp Thr Phe Ser Ser Tyr Thr
1               5

<210> SEQ ID NO 8
<211> LENGTH: 8
<212> TYPE: PRT
<213> ORGANISM: Artificial Sequence
<220> FEATURE:
<223> OTHER INFORMATION: 12-042 HCDR2
```

```
<400> SEQUENCE: 8

Ile Ile Pro Ile Phe Gly Thr Ala
1               5

<210> SEQ ID NO 9
<211> LENGTH: 18
<212> TYPE: PRT
<213> ORGANISM: Artificial Sequence
<220> FEATURE:
<223> OTHER INFORMATION: 12-042 HCDR3

<400> SEQUENCE: 9

Ala Arg Gly Pro Asp Asn His Ser Asp Arg Tyr Phe Tyr Tyr Gly Met
1               5                   10                  15

Asp Val

<210> SEQ ID NO 10
<211> LENGTH: 8
<212> TYPE: PRT
<213> ORGANISM: Artificial Sequence
<220> FEATURE:
<223> OTHER INFORMATION: 12-044 HCDR1

<400> SEQUENCE: 10

Gly Gly Ala Phe Arg Thr Ser Val
1               5

<210> SEQ ID NO 11
<211> LENGTH: 8
<212> TYPE: PRT
<213> ORGANISM: Artificial Sequence
<220> FEATURE:
<223> OTHER INFORMATION: 12-044 HCDR2

<400> SEQUENCE: 11

Ile Ile Pro Thr Leu Asp Thr Ala
1               5

<210> SEQ ID NO 12
<211> LENGTH: 20
<212> TYPE: PRT
<213> ORGANISM: Artificial Sequence
<220> FEATURE:
<223> OTHER INFORMATION: 12-044 HCDR3

<400> SEQUENCE: 12

Ala Thr Asp Tyr Gly Gly Asn Ser Asp Arg Leu Gly Ser Tyr Ser Phe
1               5                   10                  15

Ala Phe Asp Val
            20

<210> SEQ ID NO 13
<211> LENGTH: 6
<212> TYPE: PRT
<213> ORGANISM: Artificial Sequence
<220> FEATURE:
<223> OTHER INFORMATION: 12-040 LCDR1

<400> SEQUENCE: 13

Gln Ser Val Arg Ser Tyr
1               5
```

```
<210> SEQ ID NO 14
<211> LENGTH: 3
<212> TYPE: PRT
<213> ORGANISM: Artificial Sequence
<220> FEATURE:
<223> OTHER INFORMATION: 12-040 LCDR2

<400> SEQUENCE: 14

Asp Ala Ser
1

<210> SEQ ID NO 15
<211> LENGTH: 9
<212> TYPE: PRT
<213> ORGANISM: Artificial Sequence
<220> FEATURE:
<223> OTHER INFORMATION: 12-040 LCDR3

<400> SEQUENCE: 15

Gln Gln Arg Ser Asn Trp Pro Ile Thr
1               5

<210> SEQ ID NO 16
<211> LENGTH: 11
<212> TYPE: PRT
<213> ORGANISM: Artificial Sequence
<220> FEATURE:
<223> OTHER INFORMATION: 12-041 LCDR1

<400> SEQUENCE: 16

Gln Ser Leu Leu His Ser Asn Gly Tyr Asn Tyr
1               5                   10

<210> SEQ ID NO 17
<211> LENGTH: 3
<212> TYPE: PRT
<213> ORGANISM: Artificial Sequence
<220> FEATURE:
<223> OTHER INFORMATION: 12-041 LCDR2

<400> SEQUENCE: 17

Leu Gly Ser
1

<210> SEQ ID NO 18
<211> LENGTH: 9
<212> TYPE: PRT
<213> ORGANISM: Artificial Sequence
<220> FEATURE:
<223> OTHER INFORMATION: 12-041 LCDR3

<400> SEQUENCE: 18

Met Gln Ala Leu Gln Thr Pro Leu Thr
1               5

<210> SEQ ID NO 19
<211> LENGTH: 11
<212> TYPE: PRT
<213> ORGANISM: Artificial Sequence
<220> FEATURE:
<223> OTHER INFORMATION: 12-042 LCDR1

<400> SEQUENCE: 19

Gln Ser Leu Leu His Ser Thr Gly Asn Asn Tyr
1               5                   10
```

```
<210> SEQ ID NO 20
<211> LENGTH: 3
<212> TYPE: PRT
<213> ORGANISM: Artificial Sequence
<220> FEATURE:
<223> OTHER INFORMATION: 12-042 LCDR2

<400> SEQUENCE: 20

Leu Gly Ser
1

<210> SEQ ID NO 21
<211> LENGTH: 9
<212> TYPE: PRT
<213> ORGANISM: Artificial Sequence
<220> FEATURE:
<223> OTHER INFORMATION: 12-042 LCDR3

<400> SEQUENCE: 21

Met Gln Ala Leu Gln Thr Pro Arg Thr
1               5

<210> SEQ ID NO 22
<211> LENGTH: 8
<212> TYPE: PRT
<213> ORGANISM: Artificial Sequence
<220> FEATURE:
<223> OTHER INFORMATION: 12-044 LCDR1

<400> SEQUENCE: 22

Ser Ser Asn Ile Gly Ser Asn Thr
1               5

<210> SEQ ID NO 23
<211> LENGTH: 3
<212> TYPE: PRT
<213> ORGANISM: Artificial Sequence
<220> FEATURE:
<223> OTHER INFORMATION: 12-044 LCDR2

<400> SEQUENCE: 23

Ser Asn Asn
1

<210> SEQ ID NO 24
<211> LENGTH: 11
<212> TYPE: PRT
<213> ORGANISM: Artificial Sequence
<220> FEATURE:
<223> OTHER INFORMATION: 12-044 LCDR3

<400> SEQUENCE: 24

Ala Ala Trp Asp Asp Ser Leu Asn Gly Trp Val
1               5                  10

<210> SEQ ID NO 25
<211> LENGTH: 128
<212> TYPE: PRT
<213> ORGANISM: Artificial Sequence
<220> FEATURE:
<223> OTHER INFORMATION: 12-040 HC VARIABLE REGION

<400> SEQUENCE: 25

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Asn Tyr
            20                  25                  30
```

```
Tyr Ile Asn Trp Val Arg Gln Ala Pro Gly Gln Gly Leu Glu Trp Met
            35                  40                  45

Gly Arg Ile Asn Pro Leu His Gly Gly Thr Gly Phe Ala Glu Lys Phe
 50                  55                  60

Gln Gly Arg Leu Thr Met Thr Arg Asp Thr Ser Thr Ser Thr Val Asp
 65                  70                  75                  80

Met Glu Leu Ser Ser Leu Arg Ser Glu Asp Thr Ala Ile Tyr Tyr Cys
                 85                  90                  95

Val Lys Glu Arg Asp Thr Thr Met Ala Thr Asp Tyr Tyr Gly Arg Ser
                100                 105                 110

Gly Cys Phe Asp Tyr Trp Gly Gln Gly Thr Leu Val Thr Val Ser Ser
            115                 120                 125

<210> SEQ ID NO 26
<211> LENGTH: 107
<212> TYPE: PRT
<213> ORGANISM: Artificial Sequence
<220> FEATURE:
<223> OTHER INFORMATION: 12-040 LC VARIABLE REGION

<400> SEQUENCE: 26

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Arg Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Ser Leu Thr Ile Ser Ser Leu Glu Pro
 65                  70                  75                  80

Glu Asp Phe Ala Val Tyr Tyr Cys Gln Gln Arg Ser Asn Trp Pro Ile
                 85                  90                  95

Thr Phe Gly Gln Gly Thr Arg Leu Glu Ile Lys
            100                 105

<210> SEQ ID NO 27
<211> LENGTH: 131
<212> TYPE: PRT
<213> ORGANISM: Artificial Sequence
<220> FEATURE:
<223> OTHER INFORMATION: 12-041 HC VARIABLE REGION

<400> SEQUENCE: 27

Glu Val Gln Leu Val Gln Ser Gly Ala Glu Val Lys Lys Pro Gly Ala
 1               5                  10                  15

Ser Val Lys Val Ser Cys Lys Ala Ala Gly Tyr Thr Phe Thr Asn Tyr
                20                  25                  30

Tyr Leu His Trp Val Arg Gln Ala Pro Gly Gln Gly Leu Glu Ser Met
            35                  40                  45

Gly Ile Ile Asn Pro Ser Ser Gly Gly Thr Ile Tyr Ala Gln Lys Phe
 50                  55                  60

Gln Gly Arg Val Thr Met Thr Arg Asp Thr Ser Thr Ser Thr Val Phe
 65                  70                  75                  80

Met Glu Leu Ser Ser Leu Thr Ser Glu Asp Thr Ala Val Tyr Tyr Cys
                 85                  90                  95

Ala Arg Ala Gly Glu Gly Lys Ser Arg Phe Gly Glu Gly Lys Leu Arg
                100                 105                 110
```

```
Tyr Phe Tyr Tyr Gly Met Asp Val Trp Gly Gln Gly Thr Thr Val Thr
            115                 120                 125

Val Ser Ser
    130

<210> SEQ ID NO 28
<211> LENGTH: 112
<212> TYPE: PRT
<213> ORGANISM: Artificial Sequence
<220> FEATURE:
<223> OTHER INFORMATION: 12-041 LC VARIABLE REGION

<400> SEQUENCE: 28

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Leu Glu Ile Lys
            100                 105                 110

<210> SEQ ID NO 29
<211> LENGTH: 125
<212> TYPE: PRT
<213> ORGANISM: Artificial Sequence
<220> FEATURE:
<223> OTHER INFORMATION: 12-042 HC VARIABLE REGION

<400> SEQUENCE: 29

Glu Val Gln Leu Val Glu Ser Gly Ala Glu Val Arg Lys Pro Gly Ser
1               5                   10                  15

Ser Val Lys Val Ser Cys Thr Ala Ser Gly Asp Thr Phe Ser Ser Tyr
            20                  25                  30

Thr Ile Thr Trp Val Arg Gln Ala Pro Gly Gln Gly Leu Glu Trp Met
        35                  40                  45

Gly Glu Ile Ile Pro Ile Phe Gly Thr Ala Asn Tyr Ala Gln Lys Phe
    50                  55                  60

Gln Gly Arg Val Thr Leu Thr Ala Asp Glu Ser Thr Thr Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Pro Asp Asn His Ser Asp Arg Tyr Phe Tyr Tyr Gly Met
            100                 105                 110

Asp Val Trp Gly Gln Gly Thr Thr Val Thr Val Ser Ser
            115                 120                 125

<210> SEQ ID NO 30
<211> LENGTH: 112
<212> TYPE: PRT
<213> ORGANISM: Artificial Sequence
<220> FEATURE:
<223> OTHER INFORMATION: 12-042 LC VARIABLE REGION
```

-continued

```
<400> SEQUENCE: 30

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Asp Ile Lys
            100                 105                 110

<210> SEQ ID NO 31
<211> LENGTH: 127
<212> TYPE: PRT
<213> ORGANISM: Artificial Sequence
<220> FEATURE:
<223> OTHER INFORMATION: 12-044 HC VARIABLE REGION

<400> SEQUENCE: 31

Glu Val Gln Leu Val Gln Ser Gly Ser Glu Val Arg Lys Pro Gly Ser
1               5                   10                  15

Thr Val Lys Val Ser Cys Lys Gly Ser Gly Gly Ala Phe Arg Thr Ser
            20                  25                  30

Val Ile His Trp Val Arg Gln Ala Pro Gly Gln Gly Leu Arg Trp Met
        35                  40                  45

Gly Gly Ile Ile Pro Thr Leu Asp Thr Ala Asn His Ala Gln Glu Phe
    50                  55                  60

Gln Gly Arg Ala Thr Ile Thr Ala Asp Glu Ser Thr Thr Thr Ala Tyr
65                  70                  75                  80

Leu Glu Leu Ser Ser Leu Arg Ser Glu Asp Ser Ala Val Tyr Tyr Cys
                85                  90                  95

Ala Thr Asp Tyr Gly Gly Asn Ser Asp Arg Leu Gly Ser Tyr Ser Phe
            100                 105                 110

Ala Phe Asp Val Trp Gly Gln Gly Thr Thr Val Thr Val Ser Ser
        115                 120                 125

<210> SEQ ID NO 32
<211> LENGTH: 110
<212> TYPE: PRT
<213> ORGANISM: Artificial Sequence
<220> FEATURE:
<223> OTHER INFORMATION: 12-044 LC VARIABLE REGION

<400> SEQUENCE: 32

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60
```

-continued

```
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Gln Leu Thr Val Leu
             100                 105                 110
```